(12) United States Patent
Jiang et al.

(10) Patent No.: US 10,851,334 B2
(45) Date of Patent: Dec. 1, 2020

(54) SOLID STATE BIOLOGICAL REACTION DEVICE, USAGE METHOD AND USE THEREOF

(71) Applicant: Tianjin Institute of Industrial Biotechnology, Chinese Academy of Sciences, Tianjin (CN)

(72) Inventors: Wenxia Jiang, Tianjin (CN); Xiaoran Zhang, Tianjin (CN); Yanhe Ma, Tianjin (CN)

(73) Assignee: Tianjin Institute of Industrial Biotechnology, Chinese Academy of Sciences, Tianjin (CN)

( * ) Notice: Subject to any disclaimer, the term of this patent is extended or adjusted under 35 U.S.C. 154(b) by 288 days.

(21) Appl. No.: 15/750,126

(22) PCT Filed: Aug. 4, 2016

(86) PCT No.: PCT/CN2016/093267
§ 371 (c)(1),
(2) Date: Feb. 2, 2018

(87) PCT Pub. No.: WO2017/020853
PCT Pub. Date: Feb. 9, 2017

(65) Prior Publication Data
US 2018/0223235 A1    Aug. 9, 2018

(30) Foreign Application Priority Data

Aug. 6, 2015    (CN) .......................... 2015 1 0474799

(51) Int. Cl.
*C12M 1/16*    (2006.01)
*C12M 1/04*    (2006.01)
(Continued)

(52) U.S. Cl.
CPC .............. *C12M 21/16* (2013.01); *C12M 1/04* (2013.01); *C12M 1/16* (2013.01); *C12M 23/48* (2013.01);
(Continued)

(58) Field of Classification Search
CPC .......... C12M 1/04; C12M 1/16; C12M 21/16; C12M 29/04; C12M 25/06; C12M 23/50;
(Continued)

(56) References Cited

U.S. PATENT DOCUMENTS 4,868,122 A    9/1989    Kominek et al.
5,057,221 A    10/1991    Bryant et al.
(Continued)

FOREIGN PATENT DOCUMENTS

CN    1473924 A    2/2004
CN    1800337 A    7/2006
(Continued)

OTHER PUBLICATIONS

Translation of CN 201087969 Y (Year: 2008).*
International Search Report, PCT/CN2016/093267, dated Oct. 17, 2016.

*Primary Examiner* — Gautam Prakash
(74) *Attorney, Agent, or Firm* — Loza & Loza, LLP

(57) ABSTRACT

Disclosed is a solid state biological reaction device, comprising a main tank (1), wherein the device further comprises a support (2) supporting the main tank (1), and the support (2) makes the main tank (1) be rotational in the horizontal position, and be statically cultured in the vertical position. The device is relatively simple, in particular, the mixing of materials uses the method of a vehicle-tank in combination with rotation, achieving the tank free conversion between the two different poses of vertical and the horizontal; and the device conducts the work of loading, inoculation, cultivation
(Continued)

and transplantation and so on in the upright pose, and completes the work of sterilization and mixing of materials and so on in the horizontal pose. The device is not only quick to use and easy to move, but also omits the stirring system which occupies a lot of manufacturing costs, and is easy to use in large-scale production.

12 Claims, 9 Drawing Sheets

(51) Int. Cl.
*C12N 1/00* (2006.01)
*C12M 3/00* (2006.01)
*C12M 1/00* (2006.01)
*C12M 1/12* (2006.01)
*C12M 1/34* (2006.01)
*C12N 1/14* (2006.01)
*C12N 1/18* (2006.01)

(52) U.S. Cl.
CPC ............ *C12M 23/50* (2013.01); *C12M 25/06* (2013.01); *C12M 29/04* (2013.01); *C12M 41/12* (2013.01); *C12N 1/00* (2013.01); *C12N 1/14* (2013.01); *C12N 1/18* (2013.01)

(58) Field of Classification Search
CPC ......... C12M 23/48; C12M 41/12; C12N 1/00; C12N 1/14; C12N 1/18
See application file for complete search history.

(56) References Cited

U.S. PATENT DOCUMENTS

| | | | |
|---|---|---|---|
| 5,300,438 A | * | 4/1994 | Augspurger et al. ........................ C12M 23/52 435/290.3 |
| 5,494,574 A | | 2/1996 | Unterman et al. |
| 6,355,178 B1 | | 3/2002 | Couture et al. |
| 6,752,926 B2 | | 6/2004 | Christodoulatos et al. |
| 2002/0123125 A1 | | 9/2002 | Okada et al. |
| 2015/0166945 A1 | | 6/2015 | Andersen et al. |
| 2016/0083684 A1 | | 3/2016 | Li et al. |
| 2016/0369226 A1 | | 12/2016 | Jiang |

FOREIGN PATENT DOCUMENTS

| | | |
|---|---|---|
| CN | 101177693 A | 5/2008 |
| CN | 101220378 A | 7/2008 |
| CN | 201087969 Y | 7/2008 |
| CN | 101503713 A | 8/2009 |
| CN | 101524672 A | 9/2009 |
| CN | 201545827 U | 8/2010 |
| CN | 102924146 A | 2/2013 |
| CN | 103509712 A | 1/2014 |
| CN | 203559041 A | 4/2014 |
| CN | 103911282 A | 7/2014 |
| CN | 103911862 A | 7/2014 |
| CN | 104403986 A | 3/2015 |
| CN | 104522514 A | 4/2015 |
| CN | 104603257 A | 5/2015 |
| CN | 104630020 A | 5/2015 |
| WO | 8402518 A1 | 7/1984 |
| WO | 2015066954 A1 | 5/2015 |

* cited by examiner

SOLID STATE BIOLOGICAL REACTION DEVICE, USAGE METHOD AND USE THEREOF

TECHNICAL FIELD

The present disclosure belongs to the field of bioengineering, specifically to a solid state biological reaction device, a usage method and use thereof.

BACKGROUND

The filamentous organisms are producing strains of many fermentation products, and are widely used in industries such as antibiotic, organic acid, enzyme preparation and biopesticide industry. Spore inoculation is an inoculation method commonly used in the fermentation of filamentous organisms. In the fermentation production, the spore strains of the filamentous organisms are generally prepared by surface culture (such as solid-state culture). For example, a method of standing and intermittently inversing Erlenmeyer flask is generally for solid-state culturing to prepare bran koji spores of Aspergillus niger in citric acid industry, its brief technological process comprises: charging fresh brans into a Erlenmeyer flask and sterilizing, then putting the flask on a shelf after inoculation for stationary culture, during the culture process, the flask is inversed intermittently, at the end of culturing, drying the culture and storing for use, the culture is then inoculated into a seeding tank or a fermenter in use.

According to an annual output of citric acid of about 1.0-1.2 million tons in China in recent years, it is estimated that more than one million flasks of bran koji spores are required annually. However, there are some problems difficult to solve in culturing the bran koji spores with a large amount of Erlenmeyer flasks in a large-scale production, for example: a very large thermostatic koji-making chamber is needed; a large quantity of manual labor during the preparation process is needed, which consumes a lot of manpower; it is difficult to detect the quality and contamination situation of spores flask-by-flask, the batch stability of spores is not easy to control; the bran koji is susceptible to contamination during preservation; and problems during the inoculation process such as large quantity of labor, time-consuming and high risk of contamination. It can be seen from the above that since mechanization has not yet been realized in the production process of bran koji spores, and a manual operation for seed production has low production efficiency, a large scale technique for the production of filamentous organism spores has always been a common problem needed to be solved in the fermentation industry.

A critical point for realizing the large scale production of filamentous organism spores lies in the development of a device meeting the technological requirements. However, there is no device specifically used for the large scale production of filamentous organism pure spores at domestic, and there are few enterprises that manufacture and sell such device internationally. At present, we can only find a spore box (VB Spore Box) from Vogelbusch Biocommodities GmbH (Austria) in the market. The device adopts a technical route of culturing in multilayer trays and collecting the pure spores by vacuum, and the culturing, drying and collecting of the spores are all performed in a closed system, with a production capacity of 0.8-1.4 kg of Aspergillus niger pure spores per batch and a cycle of 14 days. However, since the device uses chemical fumigation for sterilization, the sterilizing agent must be completely evacuated so as not to affect the growth of the microorganism, and the evacuated sterilizing agent is needed to be neutralized to prevent environmental pollution; the agar culture medium is sterilized separately and then aseptically transferred into a box-type culture device, which is at high risk of contamination during the transferring; the time for cleaning and preparing is long and the amount of manual labor is still large; the agar culture medium is higher in cost as well; furthermore, the collection of spores by using negative pressure will also bring a higher risk of contamination.

CN 104630020 A discloses a solid state biological reaction device for the large scale production of the spore strains of the filamentous organisms, the dry spore powder produced by this device can be used for immediate inoculation to fermenter and for aseptic preservation in a spore collection flask for a long period of time. However, for some small-scale enterprises and small-size fermenters, in order to increase the level of mechanization in the production process of the spore strains while saving investment, there is also a need for a small-size production device of the filamentous organism spores with more simple and compact structure, lower manufacturing costs and more flexibility of use. Especially, if the mixing system of the device can be simplified in the design, the manufacturing costs of the device can be saved significantly. CN 203559041 U discloses a movable wine fermenter, which is suitable for use in wine fermentation, the movement function of which is a horizontal movement that can neither realize the rotation of the fermenter attitude nor have the function of rotary mixing, therefore it is not suitable for producing the filamentous organism spores by solid state biological reaction. CN 102924146A discloses a movable drum composting reactor which is designed for use as a solid state biological reactor, a rotary mixing of which is realized via rotating the drum, but the movement mode is limited to a horizontal movement, and the rotation mode is limited to a fixed axis rotation, which can neither realize a change in space attitude of the vessel nor be suitable for producing pure-culturing spore strains of the filamentous organisms by solid state biological reaction.

In view of the above problems, it is necessary to develop a novel device for a large scale production of filamentous organism spores, which can not only realize the large scale mechanization production of spores but also solve the above problems and deficiencies.

SUMMARY

The present disclosure provides a solid state biological reaction device, a usage method and a use thereof, the objects of which are to realize a low strength mixing of the materials in a small-size solid state reactor by changing the space attitude and rotating the vessel, meanwhile satisfying different requirements of the culturing and the material mixing for the attitude of the device, and simplifying the design as well as saving costs. The present disclosure can not only be used for the large scale production of filamentous organism spores, but also for the general solid state culturing and solid state fermentation of a microorganism.

To achieve this object, the present disclosure adopts the following technical solutions:

In one aspect, the present disclosure provides a solid state biological reaction device comprising a main tank, the device further comprises a support for supporting the main tank, the support can change the attitude of the main tank, so that the main tank can rotate at a horizontal position and to achieve stationary culture at a vertical position;

wherein, when the main tank is at a horizontal position, the rotation of the main tank can be achieved by manually movement or automatically driving via a driving device; and when the main tank is at a vertical position, the main tank is allowed to perform stationary culture.

In the present disclosure, a free rotation mixing of the tank in a vertical attitude and a horizontal attitude can be realized by the solid state biological reaction device of the present disclosure, and by putting down the main tank to a horizontal state, the tank can be rotated, and the rotational speed can be controlled, so that the materials within the tank can be mixed thoroughly with the inoculated strains, and a regularly rotary mixing in the subsequent culture process can be realized to make the culture uniformly grow without needing the components such as stirring paddle, and shaft seal, etc., thereby avoiding the situation of destroying the culture due to stirring the materials within the tank by a stirring paddle, etc.

Preferably, a rotary shaft is disposed at the center of the top of the main tank;

the support includes a beam for connecting to the rotary shaft of the main tank;

the support is provided with a supporting seat for supporting the main tank.

Preferably, at least one screen plate is disposed inside the main tank for holding the position of the materials.

Preferably, the opening ratio of the screen plate is from 1 to 90%, preferably from 1 to 60%.

Preferably, the outer edge of the screen plate is seal connected to the inner wall of the main tank, and the seal connecting may be a flexible seal or a rigid seal.

In the present disclosure, the screen plate may not be a full-opening screen plate, and the annular non-opening region can maintain a part of the free liquid culture medium in the side wall during the high temperature sterilization, ensuring that the culture matrix particles can fully absorb the liquid culture medium and swell, thereby ensuring that the seed solution has sufficient contact with the culture matrix and is fully absorbed during the mixing process after inoculation.

Preferably, the ratio of the diameter of the opening area of the screen plate to the outer diameter of the screen plate is from 0.1 to 1, for example can be 0.1, 0.2, 0.3, 0.4, 0.5, 0.55, 0.6, 0.7, 0.8, 0.9 or 1, preferably from 0.5 to 0.9.

Preferably, the opening in the screen plate can be but are not limited to a circular hole and/or an obround hole slot, and can also be an elliptical hole, a triangular hole, a polygonal hole, or an irregular hole.

Preferably, the diameter of the circular hole is from 0.2 to 20 mm, for example can be 0.2 mm, 0.3 mm, 0.4 mm, 0.5 mm, 0.6 mm, 0.8 mm, 1 mm, 2 mm, 3 mm, 4 mm, 5 mm, 6 mm, 8 mm, 10 mm, 12 mm, 15 mm, 16 mm, 18 mm, 19 mm or 20 mm, preferably from 0.5 to 3 mm.

Preferably, the width of the obround hole slot is from 0.2 to 20 mm, for example can be 0.2 mm, 0.3 mm, 0.4 mm, 0.5 mm, 0.6 mm, 0.8 mm, 1 mm, 2 mm, 3 mm, 4 mm, 5 mm, 6 mm, 8 mm, 10 mm, 12 mm, 15 mm, 16 mm, 18 mm, 19 mm or 20 mm, preferably from 0.5 to 3 mm.

In the present disclosure, different strains have different requirements for the ventilation rate, and the opening ratio of the screen plate can be provided according to the requirements of the strains for the ventilation rate, and the opening ratio and the aperture can be adjusted as well.

Preferably, the main tank comprises an end cap, a cylinder and a lower head arranged from top to bottom;

the end cap comprises a rotary shaft with a pin hole disposed at the center of the top of the end cap, and an off-gas filter, a liquid filter and an inoculation port disposed on the end cap;

the cylinder comprises a sight glass disposed on the inner wall of the cylinder and a temperature sensor disposed at the lower portion of the cylinder and a temperature sensor casing cased the temperature sensor;

the lower head comprises a discharge valve disposed in the middle of the bottom of the lower head and an air inlet filter disposed on the lower head.

Preferably, the sight glass has a circular shape or a stripe shape, preferably a stripe shape.

Preferably, a check valve is disposed between the air inlet filter and the lower head.

Preferably, a pipe joint is disposed at the upstream of the air inlet filter for connecting the compressed air pipeline.

Preferably, the pore diameter of the off-gas filter, the liquid filter and the air inlet filter is from 0.1 to 0.22 µm, for example can be 0.1 µm, 0.15 µm, 0.2 µm, 0.21 µm or 0.22 µm, preferably 0.2 µm.

Preferably, the main tank comprises an upper screen plate disposed at the internal junction of the end cap and the cylinder, and a lower screen plate disposed at the internal junction of the cylinder and the lower head.

In the present disclosure, the device may be provided with a set of screen plates comprising an upper screen plate and a lower screen plate, or may also be provided with multiple sets of screen plates having different diameters in the opening area, holes with different shapes and different geometrical dimensions, and different opening rate to suit different strains and materials.

Preferably, an upper spacing ring is disposed along the top edge of the cylinder, and a lower spacing ring is disposed along the top edge of the lower head.

Preferably, a jacket is disposed at the exterior of the cylinder, preferably a jacket is disposed at the exterior of the cylinder and the lower head, the jacket comprises a water inlet pipe disposed at the lower portion of the jacket and a water outlet pipe disposed at the upper portion of the jacket.

In the present disclosure, the jacket can cover all of the exposable portions of the cylinder and the lower head without any component disposed thereon, or can cover only the cylinder portion, or can cover only the lower head.

Preferably, an off-gas regulating valve is disposed between the end cap and the off-gas filter;

Preferably, an isolation valve is disposed between the end cap and the liquid filter.

Preferably, the support can change the attitude of the main tank and can be a carrier vehicle, preferably a lever-type trailer;

the lever-type trailer comprises a base and a pillar, a wheel is provided at the junction of the base and the pillar, and the base and the pillar as a whole rotates by using the axle of the wheel as a rotary shaft, the base and the pillar rotates along with the axle which can be an independent axle or can also be two axles;

the base comprises a vertical supporting leg and an annular supporting seat disposed above the base for supporting the main tank;

the pillar includes a horizontal supporting leg and a beam connected to the horizontal supporting leg for connecting to the main tank.

Preferably, a rotary driving device is disposed at the inner side of the pillar for driving the main tank to rotate.

In the present disclosure, the rotary driving device can be in electrically driving or pneumatically driving manner, and the rotational speed can be adjusted.

As a preferred embodiment, the horizontal supporting leg and the vertical supporting leg can also be a caster wheel provided with a locking means.

In the present disclosure, the horizontal supporting leg and the vertical supporting leg can be adjusted by a thread, and the stability of the main tank can be ensured when it is in a vertical position or a horizontal position.

In the present disclosure, the main tank is connected to the lever-type trailer, such that the main tank can not only change the horizontal and the vertical positions along with the lever-type trailer to facilitate the mixing of the materials and the suspension of strains; meanwhile, the main tank can be easily moved to a desired place for seed culture transferring by the lever-type trailer without additional operating steps, thereby reducing the likelihood of contamination.

Preferably, the upper surface of the annular supporting seat is provided with a sliding bearing.

Preferably, the supporting wheel is disposed at the inner side of the pillar as a side wall support for the main tank during horizontal placement and horizontal rotation.

In the present disclosure, when the device is put down to a horizontal position, the supporting wheel is used to bear the weight of the main tank while ensuring that the main tank can freely rotate, and the height of the supporting wheel can be adjusted by means of the bolts on the supporting wheel base, so that the supporting wheel is tightly fitted with the wall of the tank and can rotate in 360°.

Preferably, the beam is provided with an upright throughhole through which a sleeve for fixing the rotary shaft on the main tank is provided.

Preferably, the beam is provided with a horizontal threaded hole perpendicularly intersecting with the throughhole for mounting a fastening screw to fix the sleeve.

Preferably, the sleeve is provided with a pin hole 1 and a pin hole 2 for mounting pins for fixing.

Preferably, the inner surface of the lower end of the sleeve is provided with a sliding bearing.

Preferably, the material for making the main tank and the support is a material capable of withstanding steam sterilization at 121° C. and 0.1 MPa, and can be selected from but is not limited to any one or a mixture of at least two of stainless steel, carbon steel, nonferrous metal, light alloy, plastic, glass lining or glass.

Preferably, the end cap has an elliptical, a spherical crown, a spherical, a dished or a plated shape, preferably an elliptical or a dished shape, and further preferably an elliptical shape.

Preferably, the lower head has an elliptical, a spherical crown, a spherical, a dished or a tapered shape, preferably a tapered shape.

In the second aspect, the present disclosure provides a method for solid state culturing a microorganism using a solid state biological reaction device as described in the first aspect, the method includes the following steps:

(1) placing a granular culture matrix soaked with nutritional components of a liquid culture medium into the main tank, then sterilizing the main tank;

(2) inoculating after sterilization, putting down the main tank to a horizontal state, rotating the main tank to rotationally mix, and then setting the main tank upright to perform a thermostatic culture;

optionally, performing multiple mixing during the culturing period;

(3) after the culturing, ventilating until the culture is completely dried, and then sealed and preserved for future use;

in the present disclosure, if the strains for use in a fermenter are cultured, transferring the culture obtained after the culturing into the fermenter for culture expansion.

As a preferred embodiment, the specific steps for seed culture transferring to the fermenter include: opening the isolation valve and the off-gas regulating valve, adding water or an aqueous solution to the tank by way of filtration sterilization, thereafter closing the isolation valve and the off-gas regulating valve, putting down the main tank and performing the operation of rotary mixing continually until it is observed from the sight glass that most of the strains have been washed off. Afterwards, the main tank is put upright, the fastening screws are screwed off, and pins are inserted into the threaded hole of the beam, so that the whole main tank is suspended at a higher position. Then, a seed culture transferring pipeline is connected between the discharge valve and the inoculating valve at the top of the fermenter, and steam with a temperature of not less than 121° C. and a pressure of not less than 0.1 MPa (gauge pressure) is introduced thereto through the valves to sterilize the pipeline for at least 20 minutes. A compressed air pipeline is connected at the pipe joint and the compressed air with a pressure higher than that of the fermenter is introduced, the suspension of strains within the device is pressed into the fermenter. Alternatively, the seed culture transferring method can also be carried out according to the following steps: closing the off-gas regulating valve and the isolation valve after the seed culture transferring pipeline has been installed and sterilized, opening the discharge valve of the main tank and the inoculating valve at the top of the fermenter to make the main tank in air communication with the upper space of the fermenter, and then reducing the pressure of the fermenter, so that the suspension of strains can be transferred into the fermenter by use of differential pressure. The addition of water can be repeated for several times, such that the strains can be transferred into the fermenter as thoroughly as possible. After seed culture transferring, the inoculating valve at the top of the fermenter is closed, and the seed culture transferring pipeline is removed.

Preferably, the step (1) of the method specifically comprises the following steps:

(1a) opening the end cap and placing the granular culture matrix soaked with the nutritional components of the liquid culture medium into the main tank, then closing the end cap;

(1b) assembling and fixing the main tank and the support: fitting tightly the lower spacing ring of the main tank with the sliding bearing on the annular supporting seat of the lever-type trailer, then passing the sleeve downward through the upright through-hole on the beam to case the rotary shaft of the main tank, aligning the pin hole 2 and inserting a pin, thereafter screwing a fastening screw into the beam through the threaded hole and tightening up to withstand the sleeve, so as to tighten the sleeve and the beam as a whole;

(1c) putting down the main tank to a horizontal state along with the lever-type trailer, opening the off-gas regulating valve and the isolation valve for sterilization.

Preferably, the step (2) of the method specifically comprises the following steps:

(2a) after sterilization, inserting a compressed air pipeline at the pipe joint, blow-drying the air inlet filter, the off-gas filter and the liquid filter by introducing compressed air, meanwhile cooling the culture matrix, closing the isolation valve, slightly opening the off-gas regulating valve, and inoculating liquid strains of the microorganism to be cultured through the inoculation port under the protection of flame;

(2b) after the inoculation, putting down the main tank to a horizontal state along with the lever-type trailer, pulling out the pin of the pin hole, rotating the main tank manually so that the materials in the tank are mixed thoroughly with the inoculated suspension of the liquid strains;

(2c) re-inserting the pin after mixing, setting the main tank upright and introducing compressed air for culturing, then inducing thermostatic water with the same temperature as the culturing temperature into the jacket through the water inlet pipe and the water outlet pipe to maintain the temperature of the culture;

(2d) putting down the main tank intermittently during the culturing process, repeating the rotary mixing for multiple times;

(2e) after the culturing, compressed air can be introduced from the pipe joint to blow-dry the culture.

In the third aspect, the present disclosure provides a use of the solid state biological reaction device as described in the first aspect in the culturing of a microorganism or solid state fermentation by employing the method as described in the second aspect.

The reaction device of the present disclosure can not only be used for a large scale production of filamentous organism spores, but also for the general solid state culturing and solid state fermentation of a microorganism.

In the present disclosure, the microorganism can be selected from but is not limited to filamentous organisms, yeasts or bacteria.

Compared with the prior art, the present disclosure has the following beneficial effects:

(1) the device of the present disclosure is relatively simple, in particular a way of combining a vehicle-mounted tank with rotation is adopted for the mixing of the materials, which realizes the free rotation mixing of the tank in both the vertical attitude and the horizontal attitude;

(2) the screen plate of the device of the present disclosure is a non-full-opening screen plate used to fix the position of the materials and the strains when the main tank body is in a horizontal position, restricting the movement of the materials and the strains so that the mixing of the materials and the strains is more uniform;

(3) the device of the present disclosure can be used to facilitate the solid culturing of a microorganism, in particular the preparation of filamentous organism spores and various single cell microorganisms, and the prepared spores can be conveniently and aseptically transferred into a fermenter in the form of suspension, and can be preserved in the device for a long period of time for future use after being dried with the culture matrix. The preparation and transferring of the spores are much simpler than that of the bran koji. The prepared single cell microorganisms can also be conveniently and aseptically transferred into the fermenter in the form of the suspension of strains;

(4) the device of the present disclosure performs the operations of charging, inoculation, culturing, water addition and seed culture transferring in the vertical attitude, and the sterilization and rotary mixing of the materials in the horizontal attitude, which is not only fast-to-use and easy-to-move, but also eliminates the need for a mixing system which takes up a lot of manufacturing costs, thus having low maintenance costs.

wherein, in the figures, 1—main tank; 3—end cap; 4—tank; 5—lower head; 6—off-gas filter; 7—liquid filter; 8—inoculating port; 9—sight glass; 10—temperature sensor; 11—temperature sensor casing; 12—jacket; 13—water inlet pipe of the circulating water; 14—water outlet pipe of the circulating water; 15—air inlet filter; 16—discharge valve; 17—check valve; 18—rotary shaft; 19—pin hole; 20—upper spacing ring; 21—lower spacing ring; 22—upper screen plate; 23—lower screen plate; 24—pipe joint; 25—off-gas regulating valve; 26—isolation valve; 27—screen plate; 28—axle; 29—base; 30—annular supporting seat; 31—pillar; 32—beam; 33—horizontal supporting leg; 34—vertical supporting leg; 35—upright through-hole; 36—sleeve; 37—pin hole 1; 38—pin hole 2; 39—wheel; 40—supporting wheel; 41—threaded hole; 42—sliding bearing 1; 43—sliding bearing 2; 44—inoculating valve; 45—seed culture transferring pipeline; 46—valve; 47—valve; 48—fermenter; 49—driving device.

DETAILED DESCRIPTION

To further set forth the technical means adopted by the present disclosure and their effects, the technical solution of the present disclosure will be further illustrated with reference to the accompanying drawings and the specific embodiments, but the present disclosure is not limited to the scope of the examples.

EXAMPLE 1

A Solid State Biological Reaction Device

Figure 1:
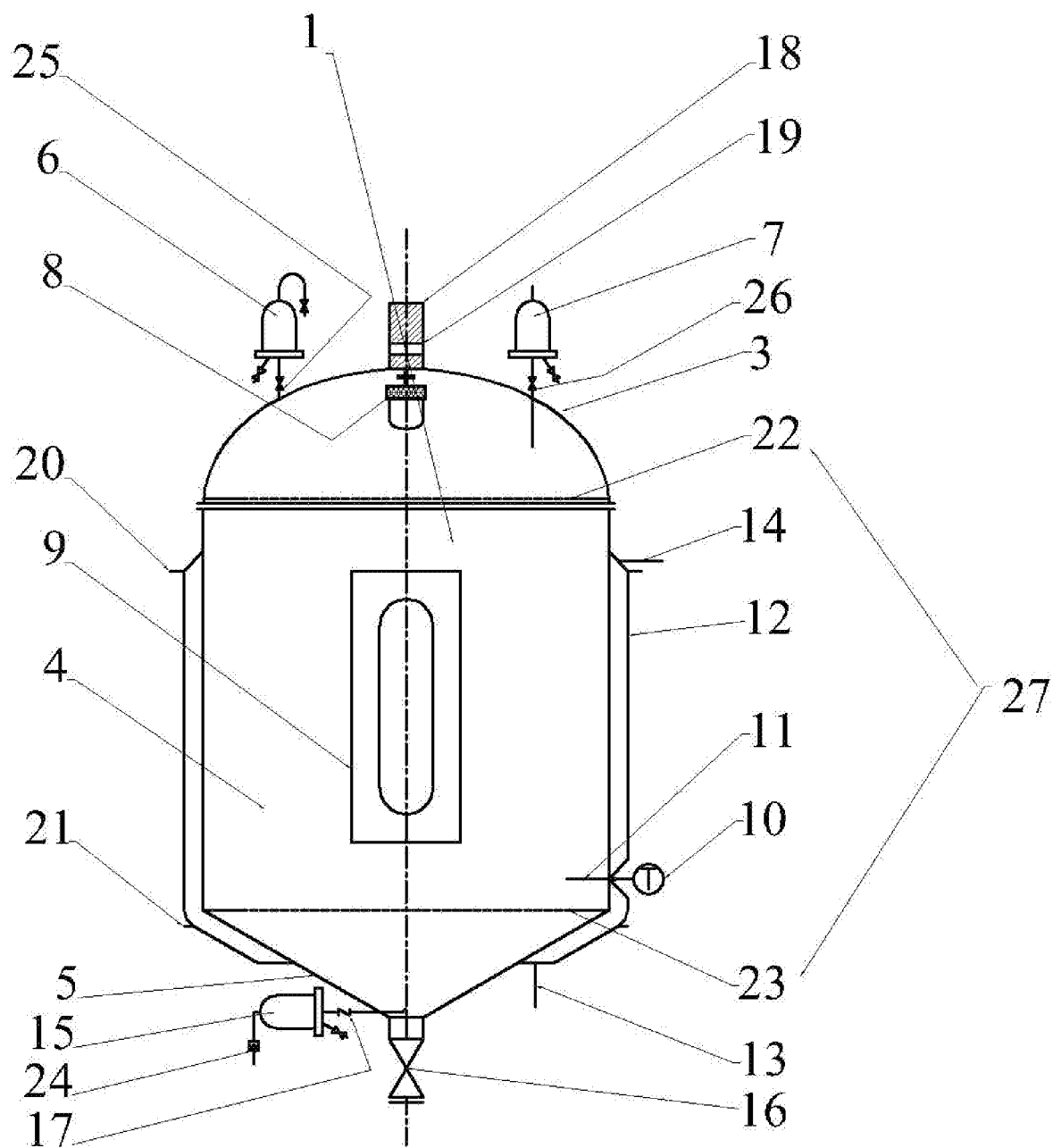
FIG. 1 is a schematic view of the main tank of the present disclosure.
Figure 2:
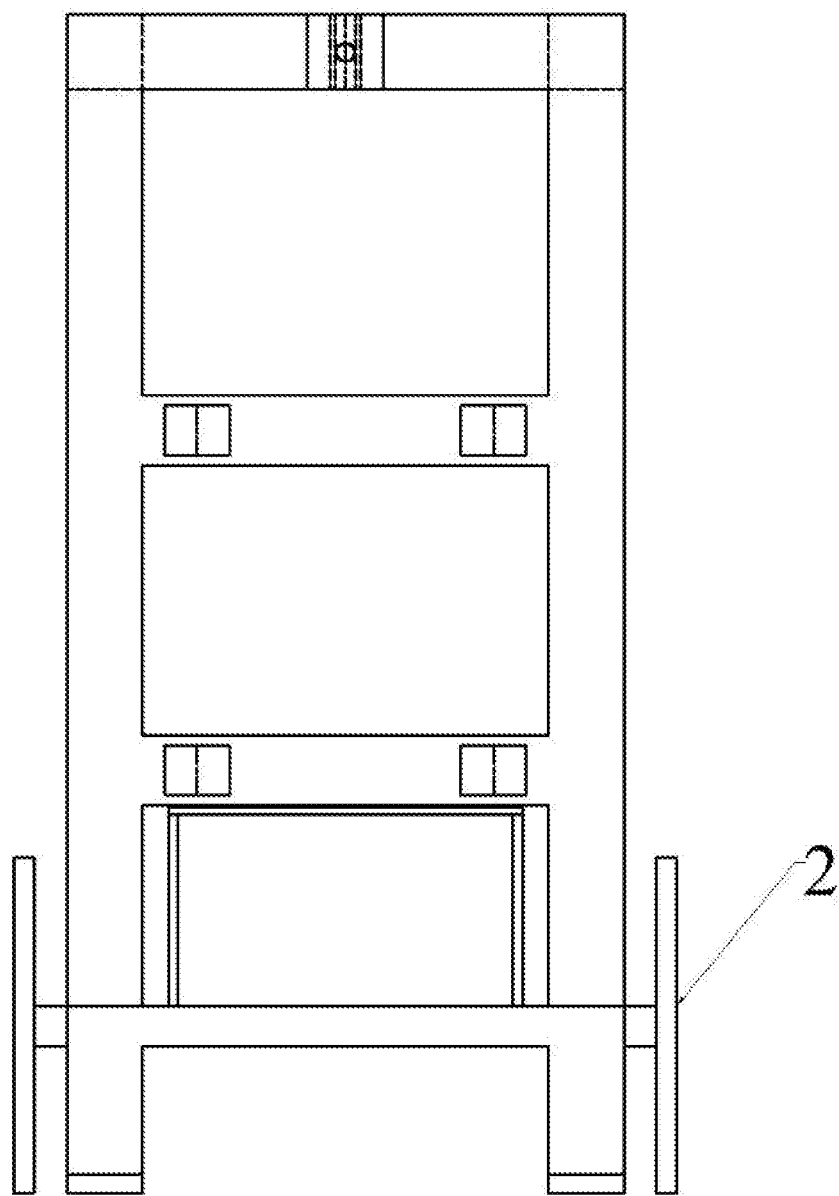
FIG. 2 is a front view of the carrier vehicle of the present disclosure.
Figure 3:
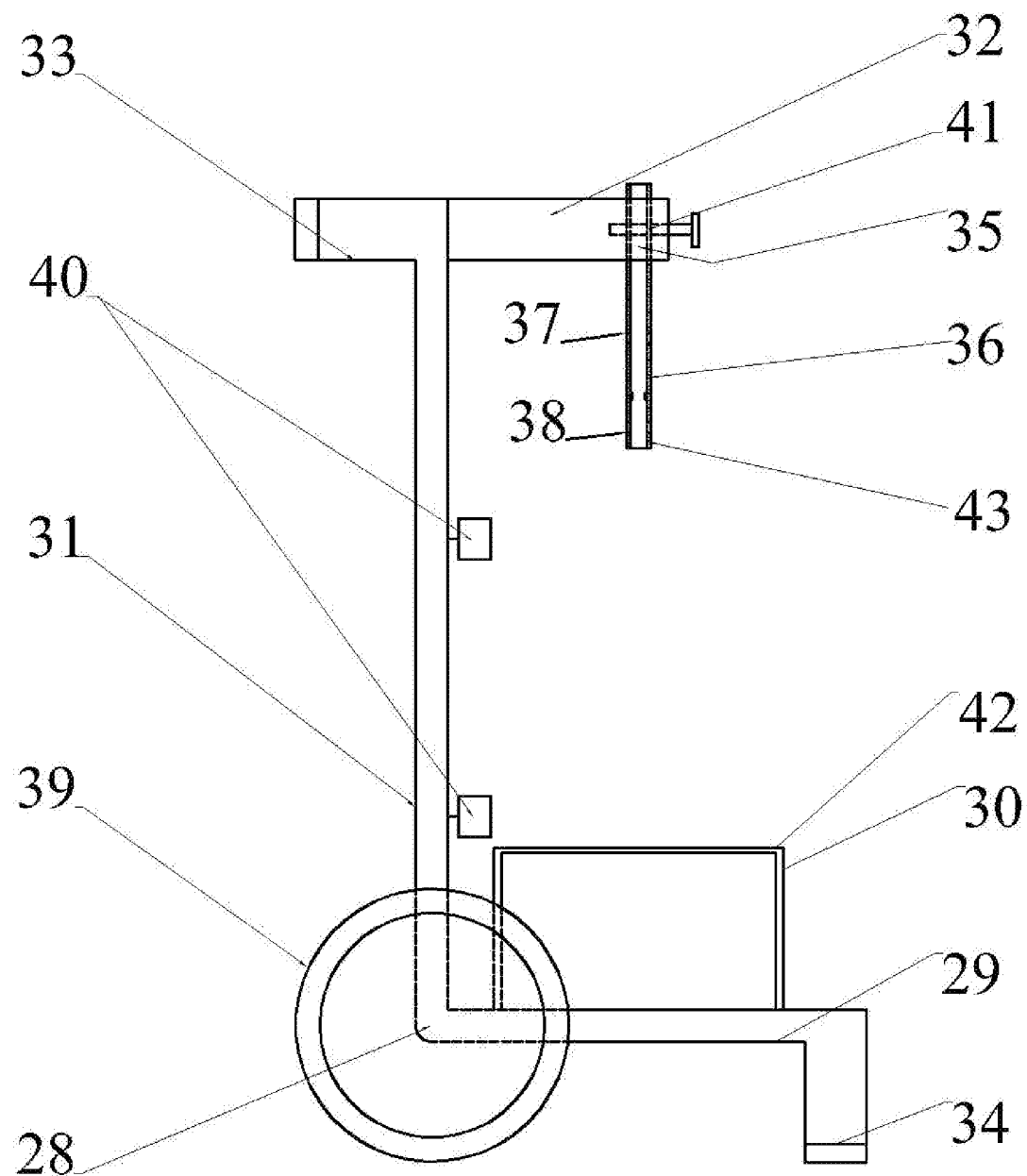
FIG. 3 is a left view of the carrier vehicle of the present disclosure.
Figure 4:
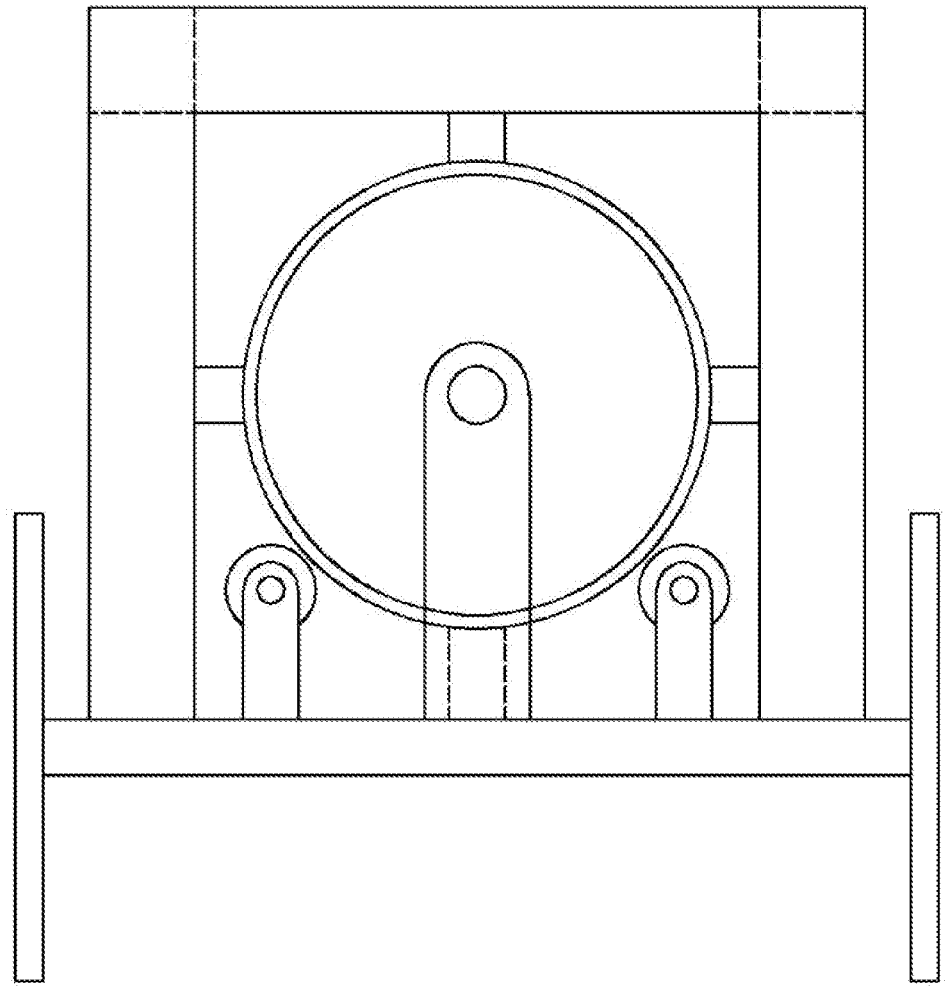
FIG. 4 is a top view of the carrier vehicle of the present disclosure.
Figure 5:
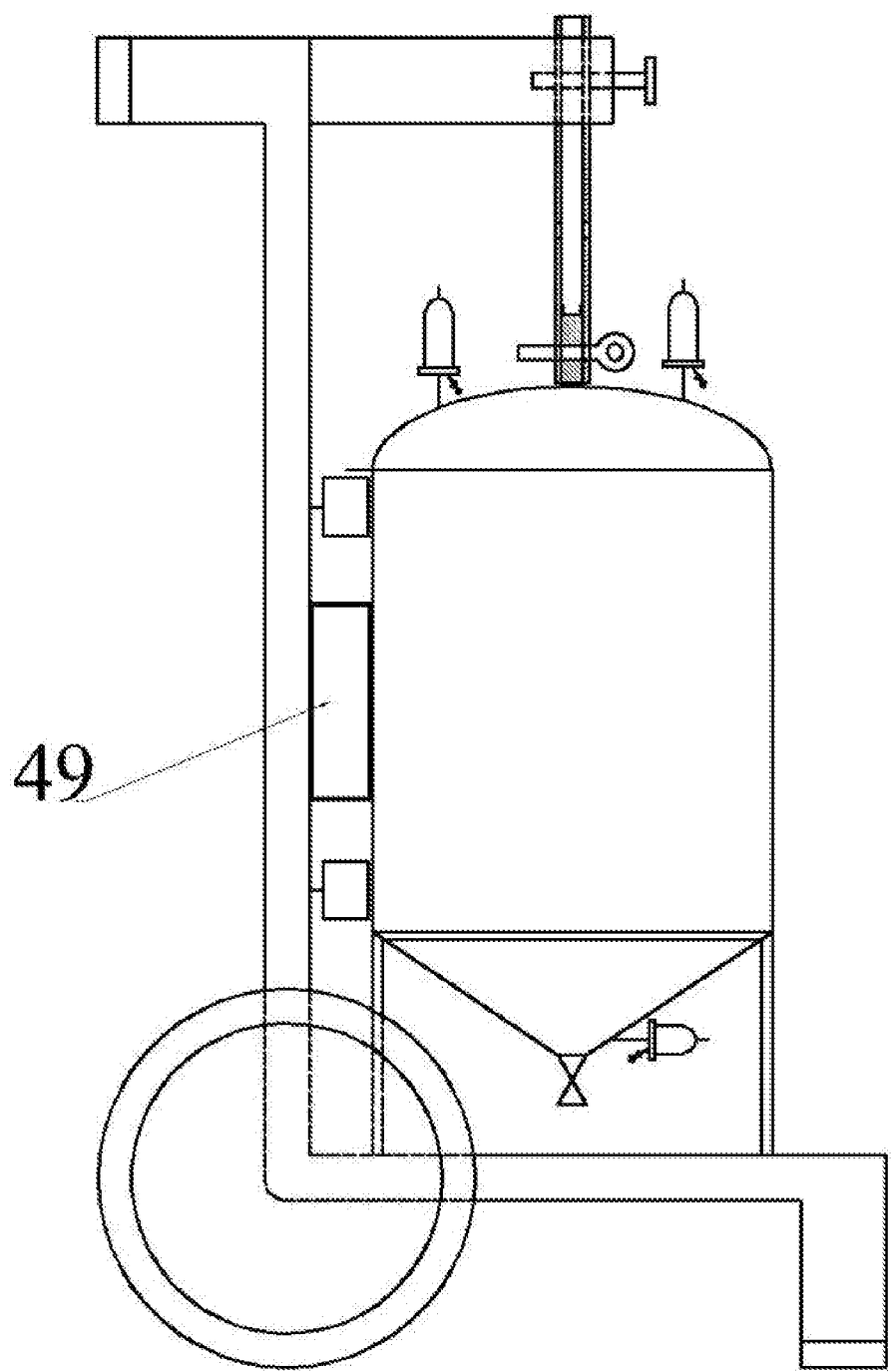
FIG. 5 is a schematic view of the inoculation/culturing state of the present disclosure.
Figure 6:
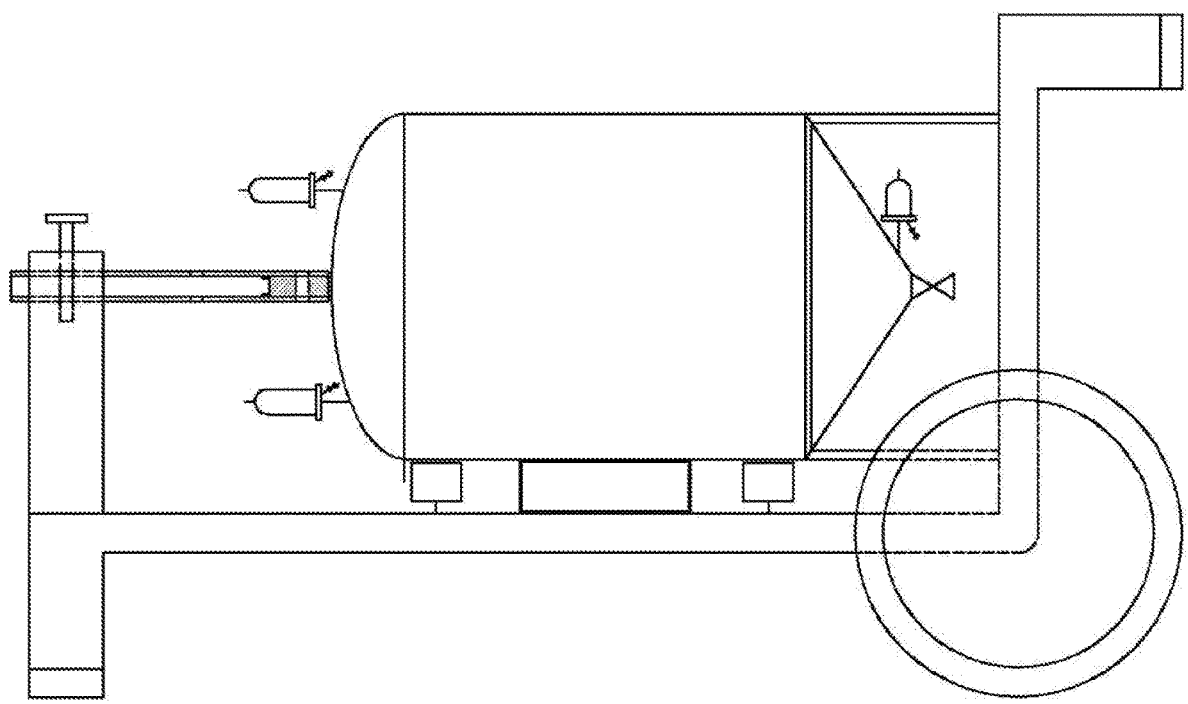
FIG. 6 is a schematic view of the sterilization/rotary mixing state of the present disclosure.
Figure 7:
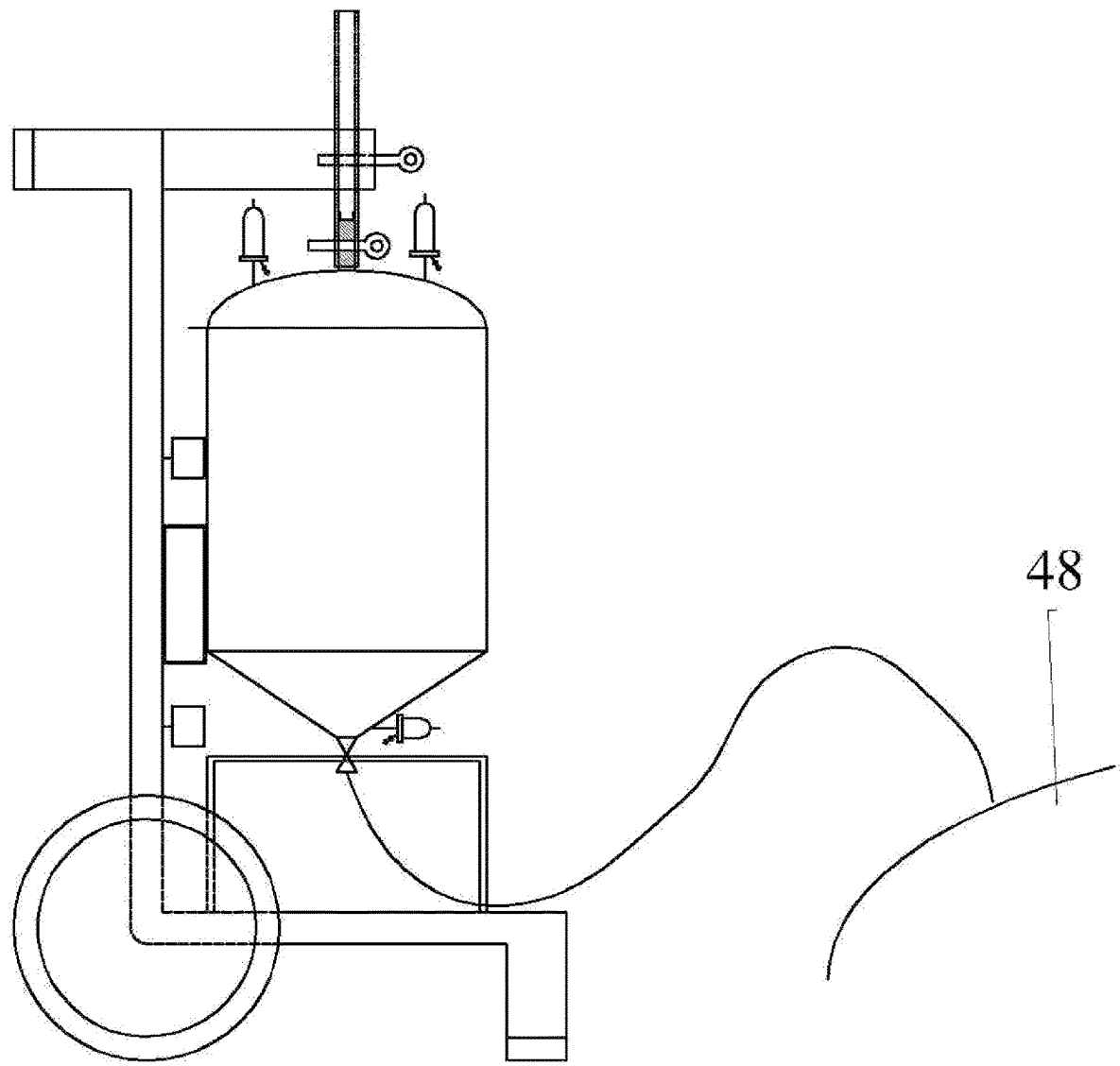
FIG. 7 is a schematic view of the seed culture transferring state of the present disclosure.
Figure 8:
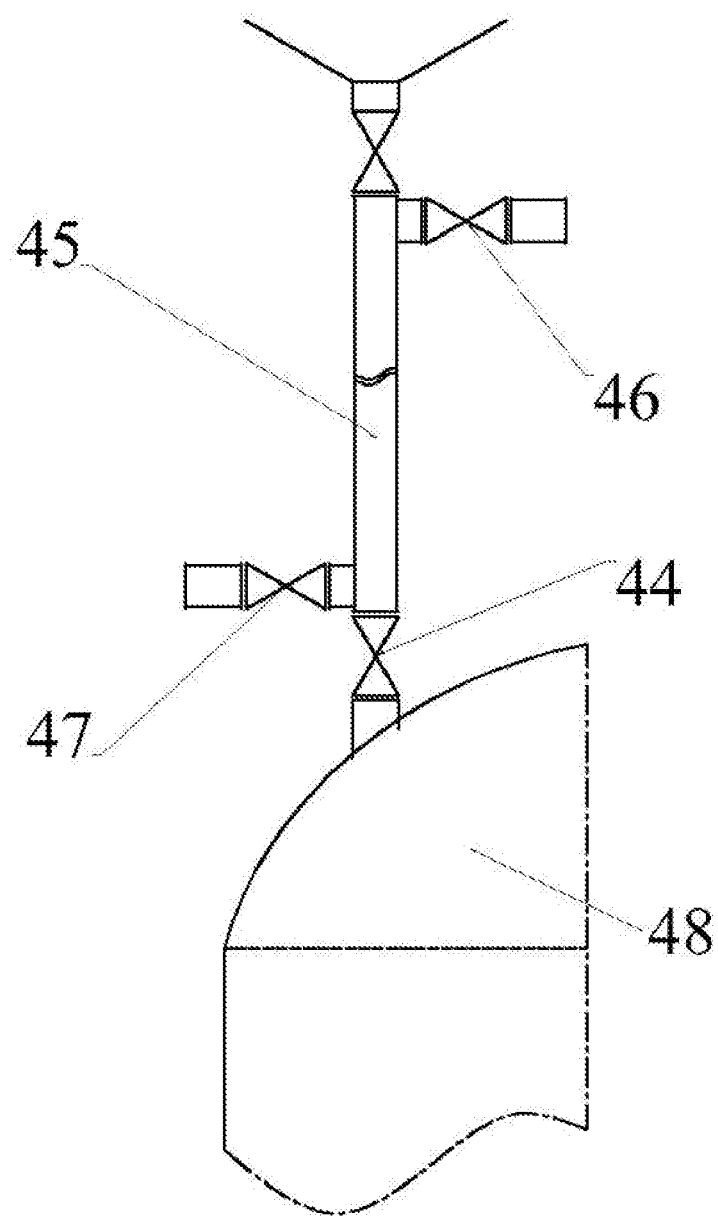
FIG. 8 is a schematic view of the four-valve seed culture transferring device of the present disclosure.
Figure 9:
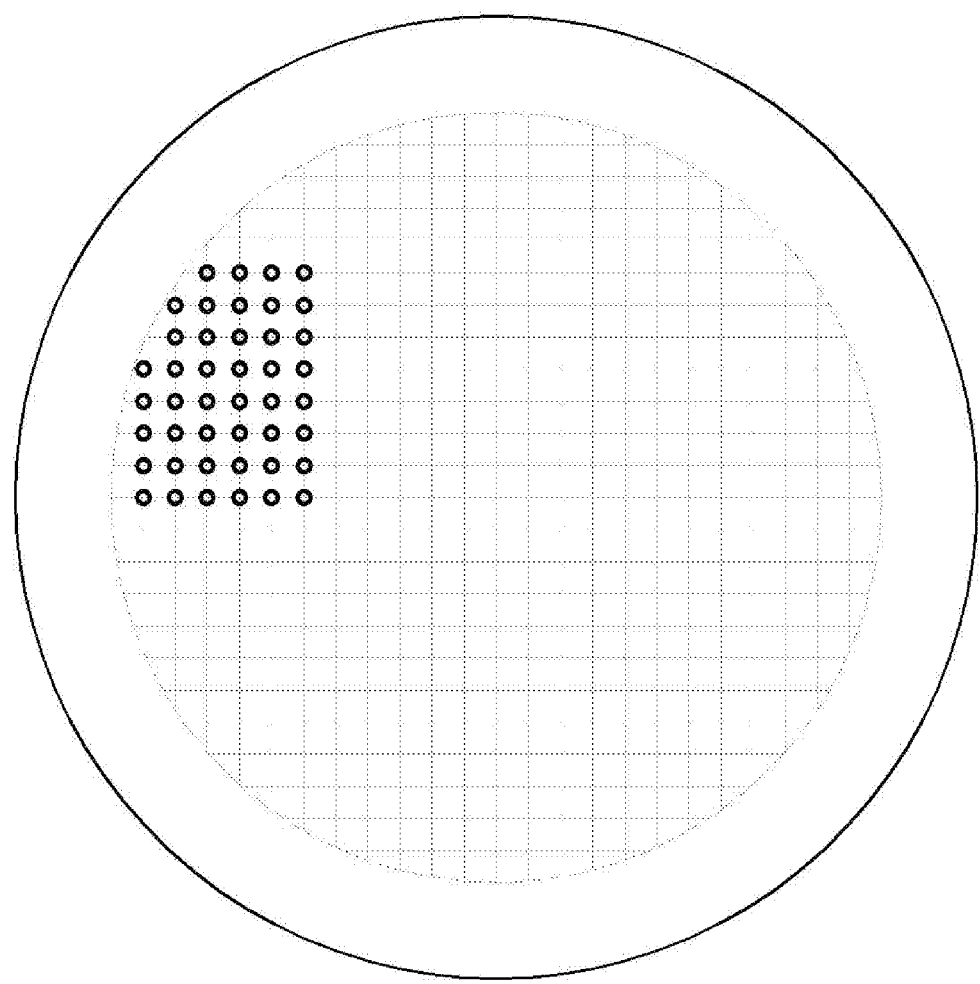
FIG. 9 is a schematic view of the screen plate and its opening region of the present disclosure.

As shown in FIG. 1, there is shown a schematic view of the solid state biological reaction device according to an embodiment of the present disclosure, the device comprises a main tank 1 and a lever-type trailer 2 which enables the main tank to rotate at a horizontal position and to achieve stationary culture at a vertical position;

wherein, when the main tank 1 is in a horizontal position, the rotation of the main tank 1 can be achieved by manually movement or automatically driving via a driving device 49; and when the main tank 1 is at a vertical position, the main tank 1 is allowed to perform stationary culture, as shown in FIG. 6.

The main tank 1 comprises an end cap 3, a cylinder 4 and a lower head 5 arranged from top to bottom;

the end cap 3 comprises a rotary shaft 18 with a pin hole 19 disposed at the center of the top of the end cap 3, and an off-gas filter 6, a liquid filter 7 and an inoculation port 8 disposed on the end cap 3; an off-gas regulating valve 25 is disposed between the end cap 3 and the off-gas filter 6; an isolation valve 26 is disposed between the end cap 3 and the liquid filter 7.

The cylinder 4 comprises a sight glass 9 disposed inside the cylinder 4 and a temperature sensor 10 disposed at the lower portion of the cylinder 4 and a temperature sensor casing 11 cased the temperature sensor 10; an upper spacing ring 20 is disposed along the top edge of the cylinder 4.

The lower head 5 comprises a discharge valve 16 disposed in the middle of the bottom of the lower head 5 and an air inlet filter 15 disposed on the lower head 5; a check valve 17 is disposed between the air inlet filter 15 and the lower head 5; a pipe joint 24 is disposed at the upstream of the air inlet filter 15 for connecting the compressed air pipeline; and a lower spacing ring 21 is disposed along the top edge of the lower head 5.

The interior of the main tank 1 comprises an upper screen plate 22 disposed at the internal junction of the end cap 3 and the cylinder 4, and a lower screen plate 23 disposed at the internal junction of the cylinder 4 and the lower head 5 to hold the position of the materials; the opening ratio of the screen plate 27 is 1-90%.

The lever-type trailer comprises a base 29 and a pillar 31, an axle 28 is provided at the junction of the base 29 and the pillar 31, and the base 29 and the pillar 31 rotates along with the axle 28, and the axle 28 is provided with a wheel 39 at both ends respectively;

the base 29 comprises a vertical supporting leg 34 and an annular supporting seat 30 disposed above the base 29 for supporting the main tank 1; the upper surface of the annular supporting seat 30 is provided with a sliding bearing 42.

The pillar 31 comprises a horizontal supporting leg 33 and a beam 32 connected to the horizontal supporting leg 33 for connecting to the main tank 4, and a supporting wheel 40 disposed at the right side of the horizontal supporting leg 33 as a side wall support for the main tank 1 during horizontal placement and horizontal rotation.

The beam 32 is provided with an upright through-hole 35 through which a sleeve 36 for fixing the rotary shaft 18 on the main tank 1 is provided; the beam 32 is provided with a horizontal threaded hole 41 perpendicularly intersecting with the through-hole 35 for mounting a fastening screw to fix the sleeve 36; the sleeve 36 is provided with a pin hole 1 (37) and a pin hole 2 (38) for mounting pins for fixing; the inner surface of the lower end of the sleeve 36 is provided with a sliding bearing 43.

The method for using the device comprises the following steps:

firstly, opening the end cap 3 and placing a granular culture matrix fully soaked with the nutritional components of a liquid culture medium into the main tank 1, then closing the end cap 3; assembling and fixing the main tank 1 and the support 2: fitting tightly the lower spacing ring 21 of the main tank 1 with the sliding bearing 42 on the annular supporting seat 30 of the lever-type trailer 2, then passing the sleeve 36 downward through the upright through-hole 35 on the beam 32 to case the rotary shaft 18 of the main tank 1, aligning the pin hole 38 then inserting a pin, thereafter screwing a fastening screw into the beam 32 through the threaded hole 41 and tightening up to withstand the sleeve 36, so as to tighten the sleeve 36 and the beam 32 as a whole; putting down the main tank 1 to a horizontal state along with the lever-type trailer 2, opening the off-gas regulating valve 25 and the isolation valve 26 for sterilization;

secondly, after sterilization, inserting a compressed air pipeline at the pipe joint 24, blow-drying the air inlet filter 15, the off-gas filter 6 and the liquid filter 7 by introducing compressed air, meanwhile cooling the culture matrix, closing the isolation valve 26, slightly opening the off-gas regulating valve 25, and inoculating liquid strains of the microorganism to be cultured through the inoculation port 8 under the protection of flame; after the inoculation, putting down the main tank 1 to a horizontal state along with the lever-type trailer 2, pulling out the pin of the pin hole 38, rotating the main tank 1 manually so that the materials in the tank are mixed thoroughly with the inoculated liquid strains; re-inserting the pin after mixing, setting the main tank 1 upright and introducing compressed air for culturing, then inducing thermostatic water with the same temperature as the culturing temperature into the jacket 12 through the water inlet pipe 13 and the water outlet pipe 14 to maintain the temperature of the culture; putting down the main tank 1 intermittently during the culturing process, repeating the rotary mixing for multiple times;

finally, transferring the culture obtained after the culturing into the fermenter 48 for culture expansion, the specific steps for seed culture transferring include: opening the isolation valve 25 and the off-gas regulating valve 26, adding water or an aqueous solution to the tank by way of filtration sterilization, thereafter closing the off-gas regulating valve 25 and the isolation valve 26, putting down the main tank 1 and performing the operation of the rotary mixing continually until it is observed from the sight glass 9 that most of the strains have been washed off. Afterwards, the main tank 1 is put upright, the fastening screws are screwed off, and pins are inserted into the threaded hole of the beam, so that the whole main tank 1 is suspended at a higher position. Then, a seed culture transferring pipeline 45 is connected between the discharge valve 16 and the inoculating valve 44 at the top of the fermenter, and steam with a temperature of not less than 121° C. and a pressure of not less than 0.1 MPa (gauge pressure) is introduced thereto through the valves 46, 47 to sterilize the pipeline for at least 20 minutes. A compressed air pipeline is connected at the pipe joint 24 and the compressed air with a pressure higher than that of the fermenter 48 is introduced, the suspension of strains within the device is pressed into the fermenter 48. The addition of water can be repeatedly for several times, such that the strains can be transferred into the fermenter 48 as thoroughly as possible. After seed culture transferring, the inoculating valve 44 at the top of the fermenter is closed, and the seed culture transferring pipeline is removed. Alternatively, the seed culture transferring method can also be carried out according to the following steps: closing the off-gas regulating valve 25 and the isolation valve 26 after the seed culture transferring pipeline 45 has been installed and sterilized, opening the discharge valve 16 at the bottom of the main tank 1 and the inoculating valve 44 at the top of the fermenter to make the main tank 1 in air communication with the upper space of the fermenter 48, and then reducing the pressure of the fermenter 48, so that the suspension of strains can be transferred into the fermenter 48 by use of differential pressure.

In Example 1, the screen plate 27 can also be disposed in the form of a plurality of layers distributed in the main tank 1, the ratio of the diameter of the opening area of the screen plate 27 to the outer diameter of the screen plate 27 is from 0.1 to 1, preferably from 0.5 to 0.9; the opening in the screen plate 27 can be a circular hole and/or an obround hole slot; the diameter of the circular hole is from 0.5 to 20 mm, preferably from 1 to 10 mm; the width of the obround hole slot is from 0.5 to 20 mm, preferably from 1 to 10 mm.

In Example 1, the sight glass 9 has a circular shape or a stripe shape, preferably a stripe shape.

In Example 1, the pore diameter of the off-gas filter 6, the liquid filter 7 and the air inlet filter 15 is from 0.2 to 0.22 preferably 0.2

In Example 1, a jacket 12 is disposed at the exterior of the cylinder 4, preferably the jacket 12 is disposed at the exterior of the cylinder 4 and the lower head 5, the jacket 12 comprises a water inlet pipe 13 disposed at the lower portion of the jacket 12 and a water outlet pipe 14 disposed at the upper portion of the jacket 12.

In Example 1, the horizontal supporting leg 33 and the vertical supporting leg 34 may also be a caster wheel provided with a height adjusting means and a locking means.

In Example 1, the material for making the main tank 1 and the carrier vehicle 2 is a material capable of withstanding steam of 121° C. and 0.1 MPa, and can be selected from but is not limited to any one or a mixture of at least two of a stainless steel, a carbon steel, a nonferrous metal, a light alloy, a plastic, a glass lining or a glass.

In Example 1, the end cap 3 has an elliptical, a spherical crown, a spherical, a dished or a plated shape, preferably an elliptical or a dished shape, and further preferably an elliptical shape.

In Example 1, the lower head 5 has an elliptical, a spherical crown, a spherical, a dished or a tapered shape, preferably a tapered shape.

EXAMPLE 2

The culturing of the spores of *Aspergillus niger* was performed by use of the device as described in Example 1 with the culturing procedure being the same as the culturing steps described in Example 1, and the components of the aqueous solution of the culture medium were as shown in Table 1, wherein the steps during the culturing were as follows:

the total volume of the main tank 1 was 30 L, the material of which was 316L stainless steel, the end cap 3 had an elliptical shape, the lower head 5 had a tapered shape with a cone apex angle of 120°, and the jacket could cover all of the exposed portions of the cylinder 4 and the lower head 5 without any accessory disposed thereon;

the screen plate 27 could also be disposed in the form of a plurality of layers distributed in the main tank 1, the opening ratio of the screen plate 27 was 29%, the ratio of the diameter of the opening area to the outer diameter of the screen plate 27 was 0.86; the opening in the screen plate 27 could be a circular hole, and the diameter of the circular hole was 3 mm.

Corncob particles having a particle size range of 5-10 mm were placed in an excess amount of an aqueous solution of the culture medium and the components of the aqueous solution of the culture medium were shown in Table 1. The saturated corncob particles were bailed from the aqueous solution of the culture medium followed by being placed on the lower screen plate and spread out to obtain a bed of material with a thickness of 10 cm, then soaked at room temperature for 12 hours, the culturing procedure was the same as the culturing steps described in Example 1, and the specific parameters were as follows: introducing thermostatic circulating water of 35° C. into the jacket continuously, keeping the culturing temperature at 35° C. and an air flow at 0.5 L/min; putting down the main tank 1 for the first time to make it in a horizontal state, rotating the main tank 1 manually with a rotation speed of 10 rpm and keeping the rotation for 10 minutes; putting down the main tank 1 again to make it in the horizontal state when culturing for 48 hours and 96 hours, respectively, with a rotation speed of 1 rpm and keeping the rotation for 2 circles; culturing for a total of 120 hours. After the culturing, the temperature of the thermostatic circulating water was raised to 38° C., and then the obtained culture was dried under an air flow of 0.5 L/min for 24 hours, afterwards, the device was stored at 25° C.

The specific steps of the seed culture transferring process were the same as those described in Example 1, and the specific parameters were as follows: after the main tank 1 was put down into the horizontal state, the rotation speed was 10 rpm and the rotation was continued for 10 minutes.

TABLE 1

| Components | Concentration (g/L) |
| --- | --- |
| Glucose | 50 |
| NaNO$_3$ | 2 |
| MgSO$_4$ 7H$_2$O | 0.5 |
| K$_2$HPO$_4$ | 1 |
| KCl | 0.5 |
| FeSO$_4$ 4H$_2$O | 0.01 |

EXAMPLE 3

The culturing of the spores of *Aspergillus* sp. was performed by use of the device as described in Example 1 with the culturing procedure being the same as the culturing steps described in Example 1, and the components of the aqueous solution of the culture medium were as shown in Table 2, wherein the steps during the culturing were as follows:

the total volume of the main tank 1 was 45 L, the material of which was 304 stainless steel, the end cap 3 had an dished shape, the lower head 5 had a spherical shape, and the jacket could cover all of the exposed portions of the cylinder 4 and the lower head 5 without any accessory disposed thereon;

the screen plate 27 could also be disposed in the form of a plurality of layers distributed in the main tank 1, the opening ratio of the upper screen plate 22 was 39%, the opening of the screen was a circular hole with a diameter of 2 mm, the ratio of the diameter of the opening area to the outer diameter of the screen plate 27 was 0.79, the opening ratio of the lower screen plate was 19%, the opening of the screen was a circular hole with a diameter of 1 mm, and the ratio of the diameter of the opening area to the outer diameter of the screen plate 27 was 1.

Corncob pieces having a particle size range of 10-20 mm were placed in an excess amount of an aqueous solution of the culture medium and the components of the aqueous solution of the culture medium were shown in Table 2. The saturated corncob pieces were bailed from the aqueous solution of the culture medium followed by being placed on the lower screen plate and spread out to obtain a bed of material with a thickness 20 cm, then soaked at room temperature for 12 hours, the culturing procedure was the same as the culturing steps described in Example 1, and the specific parameters were as follows: introducing thermostatic circulating water of 36° C. into the jacket continuously, keeping the culturing temperature at 36° C. and an air flow at 0.8 L/min; putting down the main tank 1 for the first time to make it in a horizontal state, rotating the main tank 1 by a rotary driving device 49 with a rotation speed of 10 rpm and keeping the rotation for 10 minutes; putting down the main tank 1 again to make it in the horizontal state when culturing for 36 hours and 72 hours, respectively, with the rotation speed of 1 rpm and keeping the rotation for 3 circles; culturing for a total of 96 hours. After the culturing, the temperature of the thermostatic circulating water was raised to 40° C., and then the obtained culture was dried under an air flow of 0.8 L/min for 24 h, afterwards, the device was stored at 25° C.

The specific steps of the seed culture transferring process were the same as those described in Example 1, and the specific parameters were as follows: after the main tank 1 was put down into the horizontal state, the rotation speed was 10 rpm and the rotation was continued for 10 minutes.

TABLE 2

| Components | Concentration (g/L) |
| --- | --- |
| Glucose | 40 |
| NaNO$_3$ | 1.6 |
| MgSO$_4$ 7H$_2$O | 0.4 |
| K$_2$HPO$_4$ | 0.8 |
| KCl | 0.4 |
| FeSO$_4$ 4H$_2$O | 0.008 |

EXAMPLE 4

The culturing of Saccharomyces cerevisiae. was performed by use of the device as described in Example 1 with the culturing procedure being the same as the culturing and seed culture transferring steps described in Example 1, and the components of the aqueous solution of the culture medium were as shown in Table 3.

Wherein, (1) the material of the lever-type trailer was not required to withstand the high-temperature steam; (2) only the main tank was moved into the sterilizer to sterilize when sterilization was performed, the support (2) was not sterilized; (3) the main tank 1 was rotated by a manual rotation way; (4) the temperature of the jacket was 28° C. during the culturing process; (5) the air flow introduced during the culturing process was controlled at 0.2 L/min; and (6) the culturing process was carried out for a total of 72 hours, wherein the rotary mixing was performed for 3 circles at 12 hours and 36 hours, respectively with a speed of 1 rpm.

TABLE 3

| Components | Concentration (g/L) |
| --- | --- |
| Glucose | 20 |
| Yeast extract | 10 |
| Peptone | 20 |

EXAMPLE 5

The culturing of *Bacillus subtilis*. was performed by use of the device as described in Example 1 with the culturing procedure being the same as the culturing and seed culture transferring steps described in Example 1, and the components of the aqueous solution of the culture medium were as shown in Table 4.

Wherein, (1) the shell of the tank was designed and manufactured according to the corresponding specifications of the special device pressure vessel, and a pressure gauge was installed additionally; (2) the vehicle was in the vertical state but was not put down when sterilization was performed; (3) steam with a temperature of 121° C. and a gauge pressure of 0.1 MPa was introduced into the tank from the air inlet filter for 20 minutes when sterilization was performed, the sterilizer was not used; (4) the main tank 1 was automatically rotated by a rotary driving device; (4) the temperature of the jacket was 37° C. during the culturing process; (5) the air flow introduced during the culturing process was controlled at 0.5 L/min; and (6) the culturing process was carried out for a total of 72 hours, wherein the rotary mixing was performed for 2 circles at 12 hours and 36 hours, respectively with a speed of 1 rpm.

TABLE 4

| Components | Concentration (g/L) |
| --- | --- |
| NaCl | 10 |
| Yeast extract | 5 |
| Peptone | 10 |

In conclusion, the device of the present disclosure is relatively simple, in particular a way of combining a vehicle-mounted tank with rotation is adopted for the mixing of the materials, which realizes the free rotation mixing of the tank in both the vertical attitude and the horizontal attitude; the screen plate of the device adopts a non-full-opening screen plate used to fix the position of the material and the strains when the main tank body is in a horizontal position, restricting the movement of the material and the strains so that the mixing of the material and the strains is more uniform; the device is not only fast-to-use and easy-to-move, but also eliminates the need for a mixing system which significantly saves the manufacturing costs of the device.

Applicant has stated that although the detailed methods of the present disclosure have been described by the above examples in the present disclosure, the present disclosure is not limited thereto, that is to say, it is not meant that the present disclosure has to be implemented depending on the above detailed methods. It will be apparent to those skilled in the art that any improvements made to the present disclosure, equivalent replacements and addition of adjuvant components to the raw materials of the products of the present disclosure, and selections of the specific implementations, etc., all fall within the protection scope and the disclosure scope of the present disclosure.

The invention claimed is:

1. A solid state biological reaction device comprising:
    a main tank (1), wherein the main tank (1) comprises an end cap (3) with a rotary shaft (18) which is disposed at the center of the top of the main tank (1);
    a support (2), wherein the support (2) enables the main tank (1) to rotate using the rotary shaft (18) at a horizontal position and to achieve stationary culture at a vertical position, and the support (2) comprises:
    a base (29) and a pillar (31), a wheel (39) provided at the junction of the base (29) and the pillar (31), wherein the base (29) and the pillar (31) rotate together by using the axle of the wheel (39), wherein
        the base (29) comprises a vertical supporting leg (34) and an annular supporting seat (30) disposed above the base (29) for supporting the main tank (1);
        the pillar (31) comprises a horizontal supporting leg (33) and a beam (32) connected to the horizontal supporting leg (33) for connecting to the main tank (1); and
        a beam (32) for connecting to the rotary shaft (18) of the main tank (1).

2. The solid state biological reaction device according to claim 1, wherein at least one screen plate (27) is disposed inside the main tank for holding the position of materials.

3. The solid state biological reaction device according to claim 2, wherein the screen plate has an opening ratio from 1 to 90%, wherein the ratio of the diameter of the opening area of the screen plate to the outer diameter of the screen plate is from 0.1 to 1, wherein the opening in the screen plate is a circular hole and/or an obround hole slot, wherein the diameter of the circular hole is from 0.2 to 20 mm, and the width of the obround hole slot is from 0.2 to 20 mm.

4. The solid state biological reaction device according to claim 2, wherein
the main tank further comprises a cylinder (4) and a lower head (5) wherein the end cap (3), the cylinder (4) and the lower head (5) are arranged from top to bottom;
the rotary shaft (18) comprises a pin hole (19):
the end cap (3) further comprises an off-gas filter (6), a liquid filter (7) and an inoculation port (8) disposed on the end cap (3);
the cylinder (4) comprises a sight glass (9) disposed on the inner wall of the cylinder (4) and a temperature sensor (10) disposed at the lower portion of the cylinder (4) and a temperature sensor casing (11) casing the temperature sensor (10); and
the lower head (5) comprises a discharge valve (16) disposed in the middle of the bottom of the lower head (5) and an air inlet filter (15) disposed on the lower head (5).

5. The solid state biological reaction device according to claim 4, wherein a check valve (17) is disposed between the air inlet filter (15) and the lower head (5);
wherein, a pipe joint (24) is disposed at the upstream of the air inlet filter (15) for connecting the compressed air pipeline;
wherein, the pore diameter of the off-gas filter (6), the liquid filter (7) and the air inlet filter (15) is from 0.1 to 0.22 μm.

6. The solid state biological reaction device according to claim 5, wherein the main tank (1) comprises an upper screen plate (22) disposed at the internal junction of the end cap (3) and the cylinder (4), and a lower screen plate (23) disposed at the internal junction of the cylinder (4) and the lower head (5).

7. The solid state biological reaction device according to claim 6, wherein an upper spacing ring (20) is disposed along the top edge of the cylinder (4), and a lower spacing ring (21) is disposed along the top edge of the lower head (5);
wherein, a jacket (12) is disposed at the exterior of the cylinder (4), wherein the jacket (12) comprises a water inlet pipe (13) disposed at the lower portion of the jacket (12) and a water outlet pipe (14) disposed at the upper portion of the jacket (12).

8. The solid state biological reaction device according to claim 7, wherein, the jacket (12) is disposed at the exterior of both the cylinder (4) and the lower head (5),
wherein, an off-gas regulating valve (25) is disposed between the end cap (3) and the off-gas filter (6);
wherein, an isolation valve (26) is disposed between the end cap (3) and the liquid filter (7).

9. The solid state biological reaction device according to claim 8, wherein the support (2) is a carrier vehicle.

10. The solid state biological reaction device according to claim 9, wherein, the upper surface of the annular supporting seat (30) is provided with a sliding bearing (42);
wherein, a supporting wheel (40) is disposed at the inner side of the pillar (31) as a side wall support for the main tank (1) during horizontal placement and horizontal rotation.

11. The solid state biological reaction device according to claim 10, wherein, the beam (32) is provided with an upright through-hole (35) through which a sleeve (36) for fixing the rotary shaft (18) on the main tank (1) is provided;
wherein, the beam (32) is provided with a horizontal threaded hole (41) perpendicularly intersecting with the through-hole (35) for mounting a fastening screw to fix the sleeve (36);
wherein, the sleeve (36) is provided with a first pin hole (37) and a second pin hole (38) for mounting fixed pins;
wherein, the inner surface of the lower end of the sleeve (36) is provided with a sliding bearing (43).

12. The solid state biological reaction device according to claim 11, wherein the main tank (1) is made of a material which is any one or a mixture of at least two of stainless steel, carbon steel, nonferrous metal, light alloy, plastic, glass lining or glass; and
the support (2) is made of a material which is any one or a mixture of at least two of stainless steel, carbon steel, nonferrous metal, light alloy, plastic, glass lining or glass; and
wherein, the end cap (3) has an elliptical, a spherical crown, a spherical, a dished or a plated shape; and
wherein, the lower head (5) has an elliptical, a spherical crown, a spherical, a dished or a tapered shape.

* * * * *